United States Patent
Haindl

(10) Patent No.: US 6,616,625 B2
(45) Date of Patent: *Sep. 9, 2003

(54) CATHETER FOR MEASURING CHEMICAL PARAMETERS, IN PARTICULAR FOR INTRODUCING BIOLOGICAL TISSUES, LIQUIDS OR THE LIKE

(75) Inventor: Hans Haindl, Hauptstr. 39, 30974 Wennigsen (DE)

(73) Assignee: Hans Haindl, Wennigsen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,342

(22) PCT Filed: Apr. 2, 1998

(86) PCT No.: PCT/EP98/01906
§ 371 (c)(1),
(2), (4) Date: Jan. 7, 2000

(87) PCT Pub. No.: WO98/44978
PCT Pub. Date: Oct. 15, 1998

(65) Prior Publication Data
US 2003/0060751 A1 Mar. 27, 2003

(30) Foreign Application Priority Data
Apr. 9, 1997 (DE) .......................... 197 14 572

(51) Int. Cl.$^7$ .................................. A61M 1/00
(52) U.S. Cl. ........................................ 604/27
(58) Field of Search ................ 604/27, 29–31, 604/35, 36, 39, 40, 43, 45, 264; 600/573

(56) References Cited

U.S. PATENT DOCUMENTS 5,441,481 A   8/1995   Mishra et al.

FOREIGN PATENT DOCUMENTS

| DE | 23 05 640 | 8/1975 |
|---|---|---|
| DE | 31 47 609 | 6/1983 |
| DE | 33 41 170 | 5/1984 |
| DE | 3342170 | 6/1984 |
| DE | 197 14 572 | 6/1998 |
| EP | 0401179 | 12/1990 |
| EP | 0 567 321 | 4/1993 |
| EP | 0 599 564 | 11/1993 |
| EP | 0381062 | 3/1994 |
| EP | 0 646 386 | 9/1994 |
| EP | 0 719 565 | 12/1995 |
| FR | 2655548 | 6/1991 |
| GB | 2030454 | 4/1980 |
| WO | WO 95/20991 | 8/1995 |
| WO | WO 95/33002 | 12/1995 |
| WO | WO 96/25088 | 8/1996 |

*Primary Examiner*—Brian L. Casler
*Assistant Examiner*—Ann Y. Lam
(74) *Attorney, Agent, or Firm*—Shlesinger, Arkwright & Garvey LLP

(57) ABSTRACT

A catheter used to measure chemical parameters, in particular to be inserted into biological tissue, fluids or the like, comprising a feed duct running longitudinally through the catheter to its outer end for the purpose of feeding a liquid, further a return duct running through the catheter to return the liquid and a partly permeable tubular membrane at the end of the catheter and enclosing the flow path between the end of the feed duct and the return duct. This catheter is characterized in that the feed duct (26) substantially coaxially encloses the return duct (4), or vice-versa, in that the tubular membrane (16) forms at least in the vicinity of the catheter end an inner wall (10) of the radially external return duct or the radially external feed duct (26), that the feed duct (26) and the return duct (4) communicate with each other at the catheter end by at least one radial aperture (24) and in that spacers are provided which brace the inner wall (10) of the radially external tubular part (12) and/or of the tubular membrane (16) against the external wall (6) of the inner tubular part (2).

Figure 1:
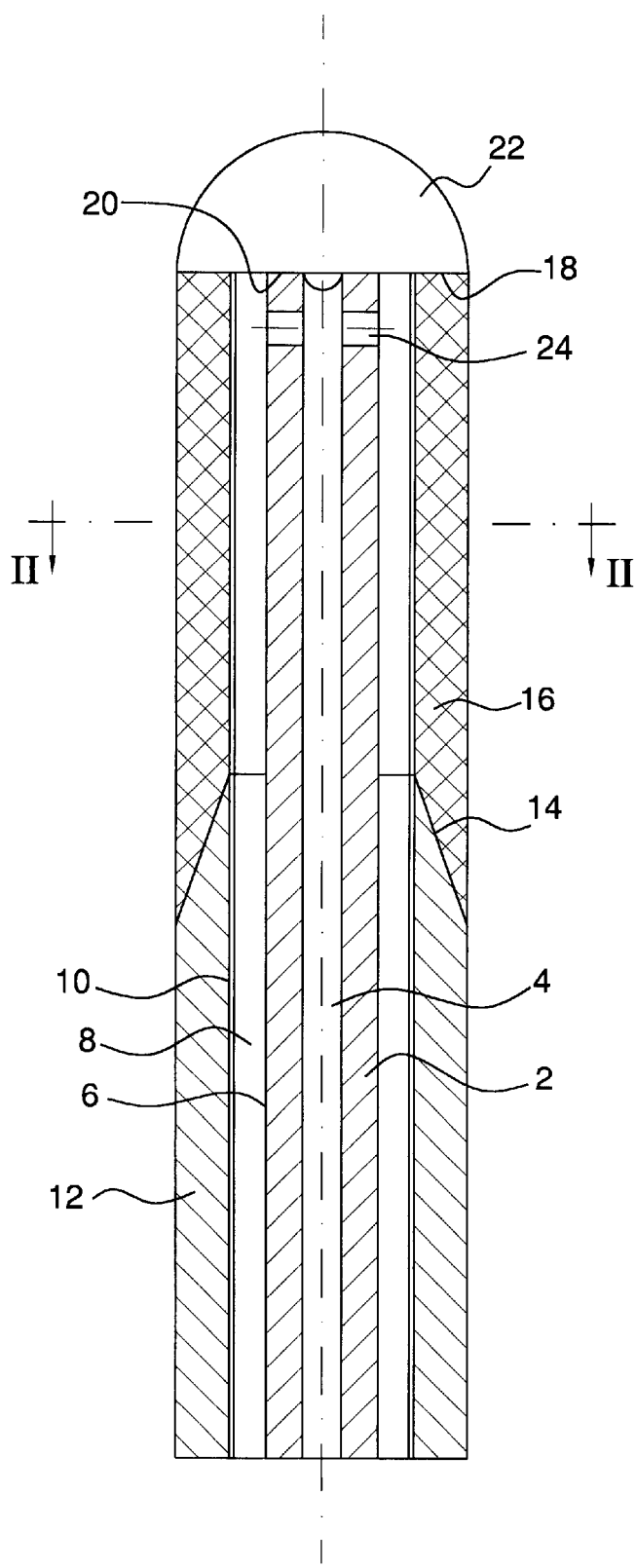

The catheter can be manufactured in simple and economical manner and makes possible a small diameter and small dead space and allows measurement without substantial time-delay at a high measurement level.

19 Claims, 2 Drawing Sheets

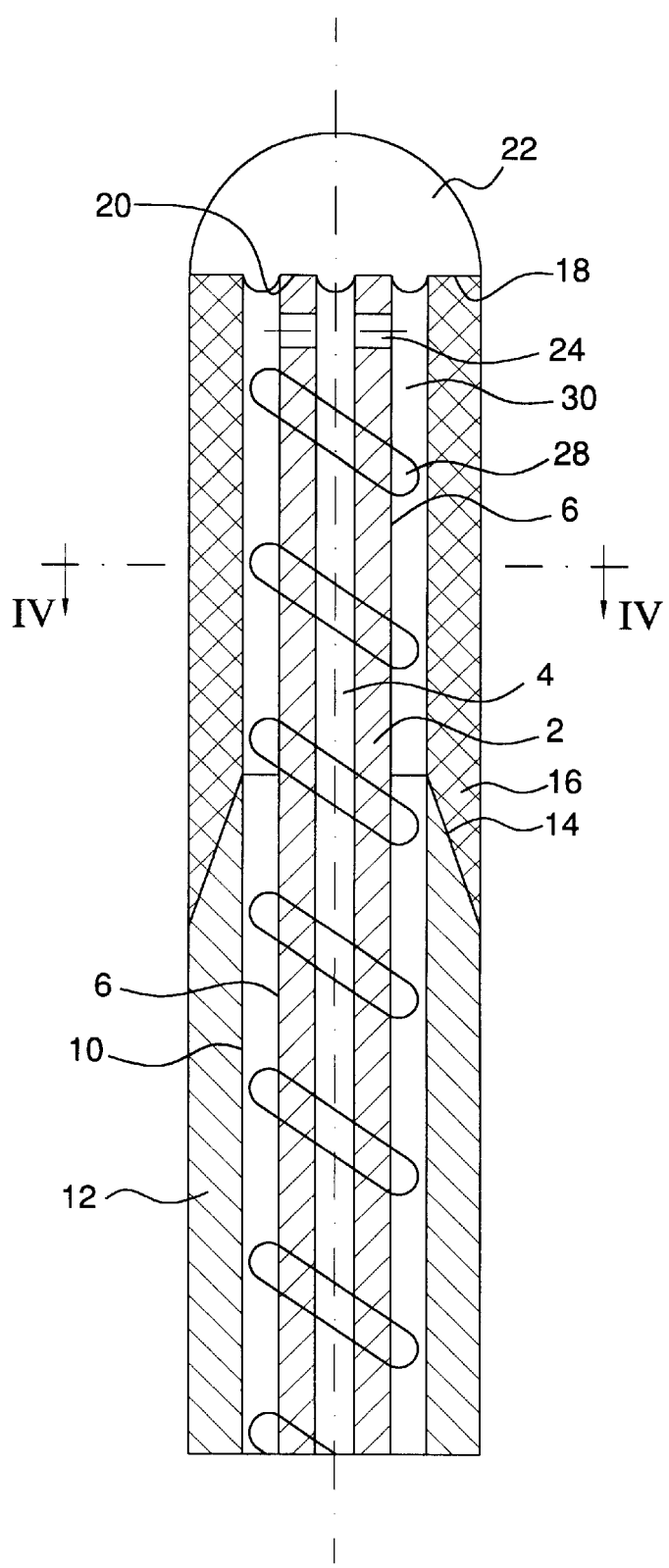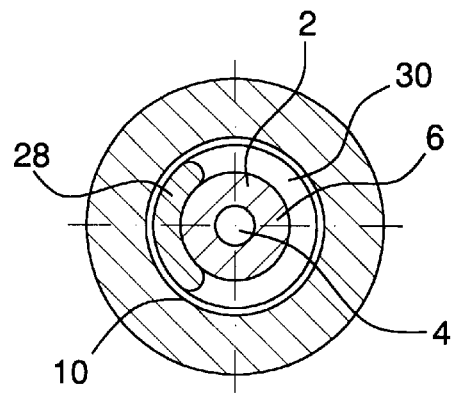
FIG.3
FIG.4

CATHETER FOR MEASURING CHEMICAL PARAMETERS, IN PARTICULAR FOR INTRODUCING BIOLOGICAL TISSUES, LIQUIDS OR THE LIKE

The invention relates to a catheter of the species named in the preamble of claim 1 to measure chemical parameters and in particular to be inserted into biological tissue, fluids or the like.

Catheters of this kind are widely known. They are called microdialysis catheters and are used to measure certain chemical parameters inside the biological tissue, usually the human body, using microdialysis. A typical example of such chemical parameters is the content in blood sugar in the subcutaneous tissue. The principle of this measurement is illustratively described in the German patent document C2 40 01 760 and in the patent document WO 95/32746 and consists in inserting a double-lumen probe, fitted at its tip with a semi-permeable portion, through the skin. A transfering solution is pumped through a duct in the catheter into this probe, flowing past the semi-permeable membrane and in the process absorbs blood sugar from the sub-cutaneous tissue. This transfering solution enriched with blood-sugar is then removed from the body through a second catheter duct and when outside said body will be mixed with a glucose/oxidase solution and fed to a sensor measuring the reaction products of the glucose oxidation reaction. Continuous measurement of blood sugar at relatively short delays is made possible by such systems.

Microdialysis probes with which to carry out the above measurements are known for instance in the patent documents U.S. Pat. No. 5,106,365 and WO 95/20983. A catheter defined in the preamble of claim 1 is known from the German patent document A1 33 42 170. It is known therein as a dialysis probe and comprises a dialysis membrane and ducts for the perfusion through the membrane. The dialysis membrane is enclosed by a housing supporting the membrane while partly being clear from it and also is more rigid than the membrane itself. The ducts are diametrically opposite within the catheter and terminate inside the tubular membrane. The relatively rigid housing serves to prevent the tubular membrane from being crushed after the catheter has been inserted into the biological tissue and thus to preserve the membrane's operation and the flow through it. Because of feature of the supporting housing, this known catheter is complex and hence expensive in its manufacture and moreover entails a comparatively large diameter. It incurs a further drawback in that the transfer flow inside the tubular membrane is non-uniform over its surface.

Aside the drawback that the partly permeable membrane is unevenly wetted by the flow of liquid and the entailed substantial restriction of the exchange surface, the probe of this species incurs the further drawback it cannot be operated under suction because in that case a reduced pressure would arise inside the tubular membrane and would cause it to collapse. When operating under pressure, a dead volume is incurred, causing the test results to be delayed. Moreover the total volume within the tubular membrane of this known probe is comparatively large and accordingly the ratio of exchange surface to volume is low and hence the concentration in drained liquid is low and measurement must be carried out at a lower level.

The objective of the invention is to create a catheter of the above kind which shall be free of the drawbacks of the state of the art, that is, which shall be manufacturable in especially simple and economical manner, of which the diameter and the dead volume shall be small, and which shall allow measurement without undue time delays and at higher measurement levels.

The task of the invention is solved by the disclosure of the features of claim 1.

The basic concept of the invention is to make the feed and return ducts in the catheter coaxial and to use the semi-permeable tubular membrane as the outer wall of the external duct at the end of the catheter. This design step already offers a low dead volume within the tubular membrane because most of the inner volume is filled by the cross-section of the inner wall of the external duct which at the same time is the external wall of the inner duct. In order to secure uniform cross-section of the external duct in spite of its small, clear width and simultaneously to prevent collapse of the tubular membrane in the region of the catheter end, another feature of the invention provides spacers mutually bracing the walls of the radially external feed duct or of the radially external return duct. A radial aperture is present at the outer catheter end to connect the inner and external ducts and as a result the external duct is reliably passing transfering liquid over the full length of the tubular membrane and effective drainage of the ingredients transmitted by the membrane from the surrounding tissue shall be assured.

The spacers may assume various designs. In one embodiment, the spacers are ribs formed on the inner wall of the external feed or return duct. The ribs maybe manufactured in very simple manner when extruding the inner catheter part. The part forming the external of the outer duct then may be pulled or pushed in the form of a tube over the inner part. However the outer and inner parts and the ribs may be extruded integrally.

In the simplest case the ribs run in the longitudinal direction of the catheter. However in especially appropriate manner the ribs shall be helical. In this manner intensive wetting of the inside surface of the semi-permeable membrane and accordingly evacuation of the ingredients transmitted by the semi-permeable membrane is assured. For a given volume of transfering liquid, the helical design of the ribs furthermore increases the flow of the transfering liquid and further the entrainment of the ingredients transmitted by the semipermeable membrane is thus made possible. Appropriately the ribs fill the full radial space of the external duct, as a result of which leakage flows between the outer edges of the ribs and the adjacent wall will be precluded.

In principle the diameter of the tubular membrane is arbitrary. In particular it may be larger than the catheter per se, for instance when the tubular membrane is slipped by its end away from that of the catheter on the catheter shank and is affixed at that place. In practice, however, the tubular membrane and the catheter appropriately shall be of approximately the same diameters.

In one suitable embodiment of the invention, the external tubular part is made of membrane material over its full length and is fitted with an impermeable layer as far as the catheter's front end zone. This design allows eliminating bonding the tubular part 12 to the membrane 16 in the region of the bonding surface 14 and hence eliminating a correspondingly complex manufacturing stage. Instead the external tubular part is made of membrane material over its full length and the single remaining manufacturing stage will be to affix the sealing layer on the inner or outer wall of the external tubular part, for instance by a simple dipping procedure.

The invention is elucidated by the illustrative embodiments discussed below.

Figure 2:
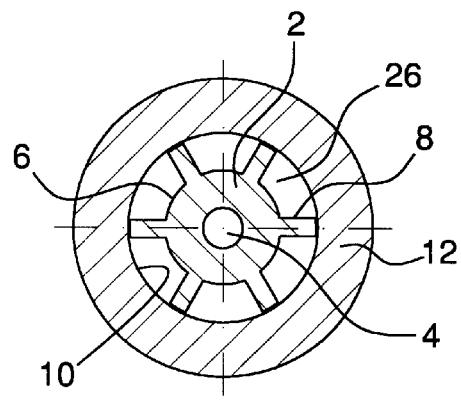

FIG. 1 shows a first illustrative embodiment of the catheter of the invention in the vicinity of its end, FIG. 2 is a section II—II through FIG. 1, FIG. 3 is a second embodiment of the invention, and FIG. 4 shows a section IV—IV of FIG. 3.

FIG. 1 shows an inner, tubular part 2 within which runs a return duct 4 for the transfering liquid. Radially directed ribs 8 are present on an external wall 6 of the tubular part 2 and tightly adjoin an inner wall 10 of an external tubular part 12. The ribs 8 were extruded jointly with the inner, tubular part 2.

The external tubular part 12 merges into a semi-permeable hose-like membrane 16 in the region of a conical bonding surface 14, the end 18 of said membrane 16 as well as an end 20 of the inner tubular part 2 being bonded to a cap 22 which might be wholly formed by a drop of glue. The outside diameter of the external tubular part in this embodiment is about 0.8 mm. The return duct 4 communicates through radial apertures 24 with a feed duct 26 formed in the region of the ribs 8 and shown in FIG. 2 which is a section II—II of FIG. 1. The segment running in the region of the hose-like membrane 16 may be termed the probe.

In use, for instance when measuring blood sugar, the catheter is inserted with the segment of hose-like membrane 16 by means of a cannula into the tissue. Thereupon transfering liquid is supplied through the feed duct 26 and then is returned through the inner return duct 4. In this process the transfering liquid flows along the inner surface of the hose-like membrane 16, the ribs 8 assuring a circumferentially uniform cross-section of the feed duct 26 and in particular preventing the semi-permeable membrane 16 from collapsing on account of externally applied pressure from the tissue on this membrane or by the reduced pressure generated by the return duct 4. The liquid flowing along the inner wall of the hose-like membrane 16 entrains the ingredients transmitted by the membrane, and these ingredients after being returned through the return duct 4 then can be measured and analyzed.

FIGS. 3 and 4 are views similar to FIGS. 1 and 2 of a variation of the embodiment of FIGS. 1 and 2. Identical or corresponding components are denoted by the same references. The difference is that in lieu of the longitudinal ribs 8 of FIG. 1, a helical rib 28 is used which rests firmly against the external wall 6 of the inner tubular part 2 or is integral with this part. A helical feed duct 30 for transfering liquid is formed between the turns of the helical rib 28, lengthening the path followed by the transfering liquid and, at constant volume, also increasing its flow in the region of the hose-like membrane 16, causing uniform wetting of the inner surface of the hose-like membrane 16 by the transfering liquid and intensive entrainment of the ingredients transmitted by this membrane.

The helical rib 28 may be implemented in arbitrary manner. Illustratively it may be in the form of a helical metal or plastic wire slipped onto the inner tubular part 2. The external tubular part 12 and the hose-like membrane thereupon will slipped over the ribs.

I claim:

1. Chemical-parameter measuring catheter for insertion into biological tissue, fluids or the like, the catheter comprising:
   a) an inner tubular part having first and second ends, said inner tubular part having a duct extending longitudinally therethrough for conveying a fluid;
   b) an external tubular part having first and second ends, said external tubular part surrounding said inner tubular part in a spaced relation therefrom to provide a duct for conveying fluid therebetween, said external tubular part duct extending between an inner wall of said external tubular part and an external wall of said inner tubular part;
   c) at least one aperture extending through said inner tubular part at one of said ends thereof to provide fluid communication between said inner tubular part duct and said external tubular part duct;
   d) a partly permeable hose-like membrane operatively associated with said external tubular part at least at one of said first and second ends thereof, said partly permeable hose-like membrane having an inner wall coextensive with said external tubular part inner wall; and
   e) a spacer, said spacer for bracing each of said permeable hose-like membrane inner wall and said external part tubular inner wall against said inner tubular part external wall and extending substantially the length of said catheter so that during measuring said external tubular part duct will be maintained open throughout.

2. Catheter as claimed in claim 1 and wherein said spacer comprises ribs on said external wall of said inner tubular part.

3. Catheter as claimed in claim 2 and wherein said ribs run in the longitudinal direction of said catheter.

4. Catheter as claimed in claim 2 and wherein said ribs are in the form of helical ribs.

5. Catheter as claimed in claim 4, and wherein said helical ribs are a separate component seated on said inner tubular part.

6. Catheter as claimed in claim 2, and wherein said ribs radially fill said external tubular part duct in such manner that a helical channel is formed therein.

7. Catheter as claimed in claim 1 and wherein said hose-like membrane having a diameter substantially equal to that of said catheter.

8. Catheter as claimed in claim 1 and wherein said external tubular part is formed of said partly permeable hose-like membrane over substantially its full length thereof and is fitted at one of said first and second ends thereof with an impermeable layer.

9. Catheter as claimed in claim 8 and wherein said impermeable layer is mounted on at least one of an exterior surface of said external tubular part and said inner wall of said exterior tubular part.

10. Catheter as claimed in claim 1 and wherein said at least one aperture has a radial configuration.

11. Chemical-parameter measuring catheter for insertion into biological tissue, fluids or the like, the catheter comprising:
   a) an inner tubular part having first and second ends, said inner tubular part having a duct extending longitudinally therethrough for conveying a fluid;
   b) an external tubular part having first and second ends, said external tubular part surrounding said inner tubular part in a spaced relation therefrom to provide a duct for conveying fluid therebetween, said external tubular part duct extending between an inner wall of said external tubular part and an external wall of said inner tubular part;
   c) at least one aperture extending through said inner tubular part at one of said ends thereof to provide fluid communication between said inner tubular part duct and said external tubular part duct;
   d) a partly permeable hose-like membrane having first and second ends and being operatively associated with said external tubular part at least at one of said first and second ends thereof, said partly permeable hose-like membrane having an inner wall coextensive with said external tubular part inner wall; and e) at least one spacer, said at least one spacer extending between said inner tubular part first and second ends to provide a brace for said partly permeable hose-like membrane inner wall and said external part tubular inner wall against said inner tubular part external wall so that during measuring said external tubular part duct will be maintained open throughout.

12. Catheter as claimed in claim 11 and wherein said at least one spacer comprises ribs on said outer wall of said inner tubular part.

13. Catheter as claimed in claim 12 and wherein said ribs run in the longitudinal direction of said catheter.

14. Catheter as claimed in claim 12 and wherein said ribs are in the form of helical ribs.

15. Catheter as claimed in claim 14, and wherein said helical ribs are a separate component seated on said inner tubular part.

16. Catheter as claimed in claim and wherein said ribs radially fill said external tubular part duct in such manner that a helical channel is formed therein.

17. Catheter as claimed in claim 11 and wherein said hose-like membrane having a diameter substantially equal to that of said catheter.

18. Catheter as claimed in claim 17 and further including an impermeable layer, said impermeable layer is mounted on at least one of an exterior surface of said external tubular part and said inner wall of said exterior tubular part.

19. Catheter as claimed in claim 11 and wherein said external tubular part is formed of said partly permeable hose-like membrane over substantially its full length thereof and is fitted at one of said first and second ends thereof with an impermeable layer.

* * * * *